United States Patent [19]

Böger et al.

[11] Patent Number: 4,550,108
[45] Date of Patent: Oct. 29, 1985

[54] 1,3,5-OXADIAZINE-2,4-DIONES AND PESTICIDAL USE

[75] Inventors: Manfred Böger, Weil am Rhein, Fed. Rep. of Germany; Jozef Drabek, Oberwil, Switzerland

[73] Assignee: Ciba Geigy Corporation, Ardsley, N.Y.

[21] Appl. No.: 639,039

[22] Filed: Aug. 9, 1984

[30] Foreign Application Priority Data

Aug. 17, 1983 [CH] Switzerland .................. 4487/83
Apr. 13, 1984 [CH] Switzerland .................. 1861/84
Jul. 13, 1984 [CH] Switzerland .................. 3424/84

[51] Int. Cl.[4] .................... A01N 43/88; C07D 413/10
[52] U.S. Cl. .................... 514/232; 514/234; 544/67
[58] Field of Search .................... 544/67; 424/248.52, 424/248.53, 248.54, 248.58, 248.57; 514/232, 234

[56] References Cited

U.S. PATENT DOCUMENTS

| | | | |
|---|---|---|---|
| 4,100,283 | 7/1978 | Kühne et al. | 424/248.5 |
| 4,150,158 | 4/1979 | Huff | 424/248.57 |
| 4,348,394 | 9/1982 | Sirrenberg et al. | 424/248.57 |
| 4,459,297 | 7/1984 | Lange et al. | 544/67 X |

Primary Examiner—Richard L. Raymond
Attorney, Agent, or Firm—Edward McC. Roberts

[57] ABSTRACT

There are disclosed novel 1,3,5-oxadiazine-2,4-diones of the formula I

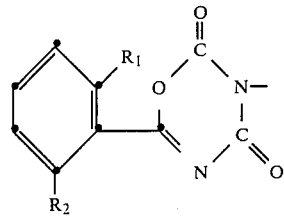

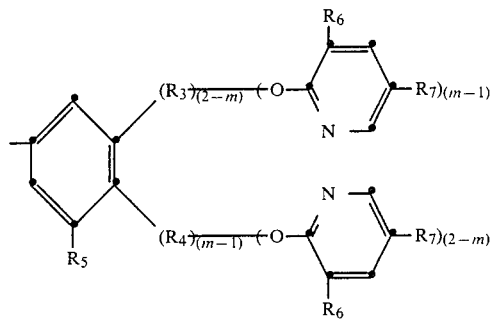

wherein
$R_1$ is halogen, $C_1$–$C_4$-alkyl, $C_1$–$C_4$-alkoxy or $C_1$–$C_4$-alkylthio,
$R_2$ is hydrogen, halogen, $C_1$–$C_4$-alkyl, $C_1$–$C_4$-alkoxy or $C_1$–$C_4$-alkylthio,
$R_3$ and $R_4$ are each hydrogen, halogen or $C_1$–$C_4$-alkyl,
$R_5$ is hydrogen, halogen, $C_1$–$C_4$-alkyl or —$COOR_8$,
$R_6$ is hydrogen or halogen,
$R_7$ is mono- or polyhalogenated $C_1$–$C_4$-alkyl,
$R_8$ is hydrogen or $C_1$–$C_4$-alkyl, and
m is 1 or 2, the production thereof, their use for controlling pests, and pesticidal compositions containing these oxadiazines as active ingredients. The preferred field of application is the control of pests on animals and plants.

17 Claims, No Drawings

1,3,5-OXADIAZINE-2,4-DIONES AND PESTICIDAL USE

The present invention relates to novel 1,3,5-oxadiazine-2,4-diones, to the production thereof, to their use for controlling pests, and to pesticidal compositions containing these oxadiazines.

The oxadiazines according to the invention correspond to the formula I

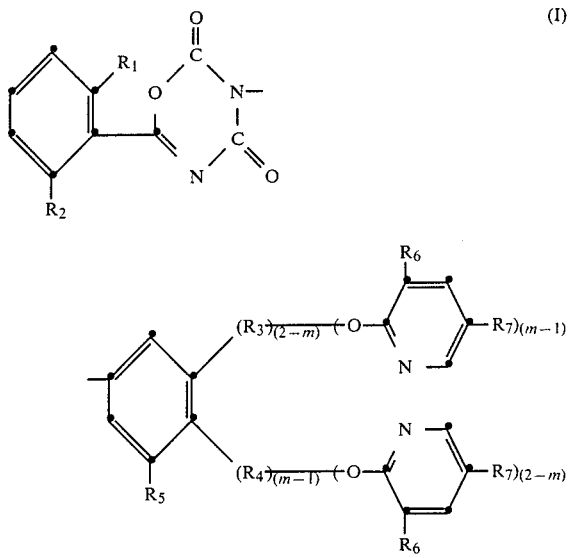

wherein $R_1$ is halogen, $C_1$–$C_4$-alkyl, $C_1$–$C_4$-alkoxy or $C_1$–$C_4$-alkylthio, $R_2$ is hydrogen, halogen, $C_1$–$C_4$-alkyl, $C_1$–$C_4$-alkoxy or $C_1$–$C_4$-alkylthio, $R_3$ and $R_4$ are each hydrogen, halogen or $C_1$–$C_4$-alkyl, $R_5$ is hydrogen, halogen, $C_1$–$C_4$-alkyl or —$COOR_8$, $R_6$ is hydrogen or halogen, $R_7$ is mono- or polyhalogenated $C_1$–$C_4$-alkyl, $R_8$ is hydrogen or $C_1$–$C_4$-alkyl, and m is 1 or 2.

Halogens suitable as substituents are both fluorine and chlorine and also bromine and iodine, the preferred halogens being fluorine and chlorine.

$C_1$–$C_4$-Alkyl, $C_1$–$C_4$-alkoxy and $C_1$–$C_4$-alkylthio groups as substituents can be straight-chain or branched-chain. Examples of such lower alkyls are: methyl, methoxy, methylthio and ethyl, ethoxy or ethylthio, as well as propyl, propoxy, propylthio and butyl, butoxy annd butylthio, and isomers thereof, preferred groups being: methyl, methoxy, methylthio and ethyl, ethoxy and ethylthio.

The definitions given for halogen and the $C_1$–$C_4$-alkyl groups apply also for the mono- or polyhalogenated $C_1$–$C_4$-alkyl groups. Examples of such haloalkyls are, inter alia: methyl which is mono- to trisubstituted by fluorine, chlorine and/or bromine; or ethyl which is mono- to pentasubstituted by fluorine, chlorine and/or bromine.

Preferred compounds of the formula I are those wherein $R_1$ is halogen or $C_1$–$C_4$-alkyl, $R_2$ is hydrogen or halogen, $R_3$ and $R_4$ are each hydrogen, halogen or $C_1$–$C_4$-alkyl, $R_5$ is hydrogen, halogen, $C_1$–$C_4$-alkyl or —$COOR_8$, $R_6$ is hydrogen or halogen, $R_7$ is mono- or polyhalogenated $C_1$–$C_4$-alkyl, $R_8$ is hydrogen or $C_1$–$C_4$-alkyl, and m is 1 or 2.

To be emphasised amongst these compounds of the formula I are those wherein $R_1$ is halogen or $C_1$–$C_4$-alkyl, $R_2$ is hydrogen or halogen, $R_3$, $R_4$ and $R_5$ are each hydrogen, halogen or $C_1$–$C_4$-alkyl, $R_6$ is hydrogen or halogen, $R_7$ is mono- or polyhalogenated $C_1$–$C_4$alkyl, and m is 1 or 2.

Particularly preferred amongst these compounds of the formula I are those wherein $R_1$ is halogen, $R_2$, $R_3$, $R_4$ and $R_5$ are each hydrogen or halogen, $R_6$ is hydrogen or chlorine, $R_7$ is $C_1$–$C_2$-alkyl which is mono- or polysubstituted by fluorine and/or chlorine, and m is 1 or 2.

And of these the compounds of the formula I to be given special mention are those wherein $R_1$ is chlorine or fluorine, $R_2$ is hydrogen or fluorine, $R_3$, $R_4$, $R_5$ and $R_6$ are each hydrogen or chlorine, $R_7$ is —$CF_3$ or —$CF_2CFCl_2$, and m is 1.

Examples of compounds of the formula I are, inter alia:

| $R_1$ | $R_2$ | $R_3$ | $R_4$ | $R_5$ | $R_6$ | $R_7$ | m |
|---|---|---|---|---|---|---|---|
| F  | H  | H      | —       | H     | H  | $CF_3$       | 1 |
| F  | F  | F      | —       | F     | F  | $CF_3$       | 1 |
| F  | Cl | Cl     | —       | Cl    | Cl | $CF_3$       | 1 |
| F  | Br | —      | Br      | H     | Br | $CBr_3$      | 2 |
| F  | F  | H      | —       | H     | Cl | $CF_2CCl_3$  | 1 |
| F  | F  | Cl     | —       | Cl    | H  | $CF_3$       | 1 |
| F  | F  | —      | n-$C_4H_9$ | H  | H  | $CF_3$       | 2 |
| Cl | H  | n-$C_4H_9$ | —   | H     | H  | $CF_3$       | 1 |
| Cl | H  | J      | —       | $C_2H_5$ | Br | $CF_2CF_3$ | 1 |
| Cl | F  | Br     | —       | Br    | H  | $CF_2CF_3$   | 1 |
| Cl | Cl | Cl     | —       | Cl    | Cl | $CCl_3$      | 1 |
| Cl | H  | H      | —       | H     | Cl | $CF_2CF_2Cl$ | 1 |
| Cl | Cl | H      | —       | H     | H  | $CF_3$       | 1 |
| Cl | H  | Cl     | —       | Cl    | H  | $CF_3$       | 1 |
| Cl | Cl | —      | i-$C_3H_7$ | H  | Br | $CF_3$       | 2 |
| Cl | H  | $C_2H_5$ | —     | H     | Cl | $CH_2CF_3$   | 1 |
| Br | Br | F      | —       | F     | H  | $CF_3$       | 1 |
| Br | J  | —      | H       | H     | Cl | $CF_3$       | 2 |
| Br | H  | —      | F       | n-$C_3H_7$ | H | $CF_3$     | 2 |

-continued

| $R_1$ | $R_2$ | $R_3$ | $R_4$ | $R_5$ | $R_6$ | $R_7$ | m |
|---|---|---|---|---|---|---|---|
| Br | F | $C_2H_5$ | — | Br | Cl | $CF_3$ | 1 |
| J | H | Br | — | H | H | $CHF_2$ | 1 |
| $CH_3$ | H | — | $CH_3$ | J | Cl | $CF_3$ | 2 |
| $CH_3$ | F | F | — | H | H | $CF_3$ | 1 |
| $CH_3$ | H | Cl | — | Cl | Cl | $CF_3$ | 1 |
| $t\text{-}C_4H_9$ | H | $n\text{-}C_3H_7$ | — | H | F | $CF_3$ | 1 |
| Cl | H | H | — | $COOC_2H_5$ | Cl | $CF_3$ | 1 |
| F | F | H | — | $COOCH_3$ | Cl | $CF_2CFCl_2$ | 1 |
| F | F | Cl | — | $COOCH_3$ | Cl | $CF_3$ | 1 |
| Cl | H | H | — | $COOC_4H_9\text{—}n$ | Cl | $CF_3$ | 1 |
| F | F | Cl | — | $COOCH_3$ | Cl | $CF_2CFCl_2$ | 1 |
| Cl | H | Br | — | $COOCH_3$ | Cl | $CF_3$ | 1 |
| $CH_3$ | Cl | H | — | $COOCH_3$ | Cl | $CF_3$ | 1 |
| F | F | H | — | COOH | Cl | $CF_3$ | 1 |
| F | F | — | H | $COOCH_3$ | Cl | $CF_3$ | 2 |
| $CH_3O$ | H | — | H | $CH_3$ | Cl | $CF_3$ | 2 |
| $CH_3O$ | F | $n\text{-}C_4H_9$ | — | F | F | $CF_3$ | 1 |
| $n\text{-}C_4H_9O$ | Cl | F | — | H | H | $CF_2CFCl_2$ | 1 |
| $CH_3O$ | $CH_3O$ | H | — | $COOCH_3$ | Cl | $CF_3$ | 1 |
| $C_3H_7O$ | $C_3H_7O$ | Cl | — | Cl | Cl | $CF_3$ | 1 |
| $i\text{-}C_3H_7O$ | H | $CH_3$ | — | H | Cl | $CF_3$ | 1 |
| $CH_3S$ | $CH_3S$ | — | H | $COOC_2H_5$ | F | $CF_3$ | 2 |
| $C_2H_5S$ | H | Cl | — | Cl | Cl | $CF_3$ | 1 |
| $CH_3S$ | $CH_3$ | H | — | H | Cl | $CF_3$ | 1 |

The compounds according to the invention can be produced by processes known per se. Such processes are described, inter alia, in the German Offenlegungsschriften Nos. 2,732,115 and 2,905,687. The compounds of the formula I can thus be obtained for example by reacting a benzoylisocyanate of the formula II

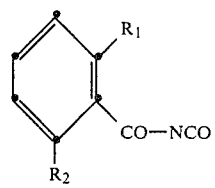
(II)

with an isocyanate of the formula III

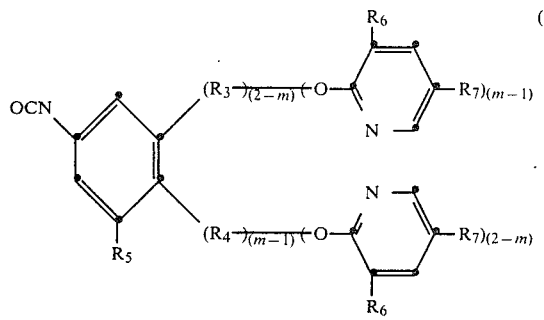
(III)

The process is carried out by heating the two reaction components, optionally in the presence of a solvent or diluent, for 30 minutes to 30 hours at a temperature within the range of 50° to 150° C., preferably for 5 to 15 hours at a temperature of between 80° and 120° C. Suitable solvents or diluents are in particular polar aprotic solvents, for example dimethyl sulfoxide dimethylformamide or N,N-dimethylacetamide.

The compounds according to the invention can however be produced also by other methods, for example (a) by condensing a halocarbonylbenzamide of the formula IV

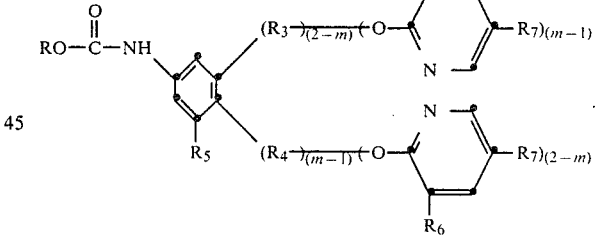
(IV)

with an isocyanate of the formula III; or (b) by condensing a benzoylisocyanate of the formula II with a carbamic acid ester of the formula V (V)

In the formulae II to V, the symbols $R_1$ to $R_7$ and m have the meanings defined for the formula I, whilst X is halogen, preferably chlorine, and R is an alkyl group, preferably a lower alkyl group having 1 to 4 carbon atoms.

The compounds of the formulae II to V are known and can be produced by known methods. Thus, the benzoylisocyanates of the formula II can be produced by reaction of the correspondingly substituted benzamides with oxalyl chloride; and the isocyanates of the formula III can be obtained from the correspondingly substituted pyridyloxyanilines by reaction with phosgene.

Whilst having favourable tolerance to warm-blooded animals and to plants, the compounds according to the invention are valuable active substances for controlling pests. The compounds of the formula I are thus suitable for example for controlling pests on animals and plants.

Such pests belong principally to the Arthropoda phylum, such as in particular insects of the orders: Lepidoptera, Coleoptera, Homoptera, Heteroptera, Diptera, Thysanoptera, Orthoptera, Anoplura, Siphonaptera, Mallophaga, Thysanura, Isoptera, Psocoptera or Hymenoptera; and Arachnida of the order Acarina, for example mites and ticks. Every development stage of the pests can be controlled, that is to say, the adults, pupae and nymphs, and also in particular the larvae and eggs. It is thus possible to effectively control especially larvae and eggs of phytopathogenic insect pests and mites in crops of ornamental plants and productive plants, for example in fruit and vegetable crops, and especially in cotton crops. When compounds of the formula I are taken up with the feed by imagines, the action of the compounds can be shown by the immediate killing of the pests, or by a reduced oviposition and/or a lessened rate of hatching. The last-mentioned effect can be observed particularly in the case of Coleoptera. In the control of zooparasitic pests, especially on domestic and productive animals, the pests concerned are above all ectoparasites, for example mites and ticks and Diptera, such as *Lucilia sericata*.

The action of the compounds according to the invention, or of compositions containing them, can be considerably broadened and adapted to suit given circumstances by the addition of other insecticides and/or acaricides. Suitable additives are for example: organic phosphorus compounds, nitrophenols and derivatives thereof, formamidines, ureas, carbamates, pyrethroids, chlorinated hydrocarbons and *Bacillus thuringiensis* preparations.

The compounds of the formula I can be combined with particular advantage also with substances which have a pesticidally intensifying effect. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I are used either in an unmodified form, or preferably together with auxiliaries customarily employed in formulation practice, and are thus processed, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of compositions, are selected to suit the objectives to be achieved and the prevailing conditions.

The formulations, that is to say, the compositions or preparations containing the active ingredient of the formula I, or combinations of this active ingredient with other insecticides and acaricides, and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, and as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acids or highly dispersed absorbent polymers.

Suitable granulated adsorptive carriers are porous types, for example: pumice, ground brick, sepiolite or bentonite; and suitable nonsorbent carriers are materials such as calcite or sand. A great number of pregranulated materials of inorganic or organic nature, such as in particular dolomite or ground plant residues, can also be used.

Depending on the nature of the active ingredient of the formula I, or of the combination of this active ingredient with other insecticides or acaricides, to be formulated, suitable surface-active compounds are: nonionic, cationic and/or anionic tensides having good emulsifying, dispersing and wetting properties. By 'tensides' are also meant mixtures of tensides.

Suitable anionic tensides are both so-called water-soluble soaps, as well as water-soluble, synthetic, surface-active compounds.

Soaps which may be mentioned are the alkali metal, alkaline-earth metal or optionally substituted ammonium salts of higher fatty acids ($C_{10}$–$C_{22}$), for example the sodium or potassium salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates.

The fatty sulfonates or sulfates are as a rule in the form of alkali metal, alkaline-earth metal or unsubstituted or substituted ammonium salts, and they generally contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included amongst these are the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols. Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per polypropylene glycol unit.

Examples of nonionic tensides which may be mentioned are: nonylphenol-polyethoxyethanols, castor oil polyglycol ethers, polypropylene/polyethylene oxide adducts, tributylphenoxy-polyethoxyethanol, polyethylene glycol and octylphenoxy-polyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethyl ammonium chloride or benzyldi-(2-chloroethyl)-ethylammonium bromide.

The tensides customarily used in formulation practice are described, inter alia, in the following publications:
"Mc Cutcheon's Detergents and Emulsifiers Annual", MC Publishing Corp., Ridgewood, N.J., 1981;
Dr. Helmut Stache "Tensid-Taschenbuch" (Tenside Manual),
Carl Hanser Verlag, Munich/Vienna, 1981.

The pesticidal preparations contain as a rule 0.1 to 99%, particularly 0.1 to 95%, of active ingredient of the formula I, or of combinations of this active ingredient with other insecticides or acaricides, 1 to 99.9% of a solid or liquid additive, and 0 to 25%, especially 0.1 to 20%, of a tenside. Whereas commercial products are preferably in the form of concentrated compositions, the products employed by the end-user are as a rule preparations having considerably lower concentrations of active ingredient.

The compositions can also contain further additives, such as stabilisers, antifoaming agents, viscosity regulators, binders and adhesives, as well as fertilisers or other active ingredients for obtaining special effects.

Formulation examples for liquid active ingredients of the formula I or combinations of these active ingredients with other insecticides or acaricides (% = percent by weight)

| 1. Emulsion concentrates | (a) | (b) | (c) |
|---|---|---|---|
| active ingredient or active-ingredient combination | 25% | 40% | 50% |
| calcium dodecylbenzenesulfonate | 5% | 8% | 6% |
| castor-oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the concentration required can be produced from such concentrates by dilution with water.

| 2. Solutions | (a) | (b) | (c) | (d) |
|---|---|---|---|---|
| active ingredient or active-ingredient combination | 80% | 10% | 5% | 95% |
| ethylene glycol monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 3. Granulates | (a) | (b) |
|---|---|---|
| active ingredient or active-ingredient combination | 5% | 10% |
| kaolin | 94% | — |
| highly dispersed silicic acid | 1% | — |
| attapulgite | — | 90% |

The active ingredient or the active-ingredient combination is dissolved in methylene chloride, the solution is sprayed onto the carrier, and the solvent is subsequently evaporated off in vacuo.

| 4. Dusts | (a) | (b) |
|---|---|---|
| active ingredient or active-ingredient combination | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient or active-ingredient combination.

Formulation examples for solid active ingredients of the formula I or combinations of these active ingredients with other insecticides or acaricides (% = percent by weight)

| 5. Wettable powders | (a) | (b) | (c) |
|---|---|---|---|
| active ingredient or active-ingredient combination | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient or the active-ingredient combination is well mixed with the additives, and the mixture is thoroughly ground in a suitable mill. Wettable powders which can be diluted with water to give suspensions of the concentration required are obtained.

| 6. Emulsion concentrate | |
|---|---|
| active ingredient or active-ingredient combination | 10% |
| octylphenol polyethylene glycol ether (4–5 mols of ethylene oxide) | 3% |
| calcium dodecylbenzene sulfonate | 3% |
| castor oil polyglycol ether (36 mols of ethylene oxide) | 4% |
| cyclohexanone | 30% |
| xylene mixture | 50% |

Emulsions of the concentration required can be obtained from this concentrate by dilution with water.

| 7. Dusts | (a) | (b) |
|---|---|---|
| active ingredient or active-ingredient combination | 5% | 8% |
| talcum | 95% | — |
| kaolin | — | 92% |

Dusts ready for use are obtained by mixing the active ingredient or active-ingredient combination with the carriers and grinding the mixture in a suitable mill.

| 8. Extruder granulate | |
|---|---|
| active ingredient or active-ingredient combination | 10% |
| sodium lignin sulfonate | 2% |
| carboxymethylcellulose | 1% |
| kaolin | 87% |

The active ingredient or the active-ingredient combination is mixed and ground with the additives, and the mixture is moistened with water. This mixture is extruded, granulated, and subsequently dried in a stream of air.

| 9. Coated granules | |
|---|---|
| active ingredient or active-ingredient combination | 3% |
| polyethylene glycol (M.W. 200) | 3% |
| kaolin | 94% |

The finely ground active ingredient or the active-ingredient combination is evenly applied, in a mixer, to the kaolin moistened with polyethylene glycol. Dust-free coated granules are obtained in this manner.

| 10. Suspension concentrate | |
|---|---|
| active ingredient or active-ingredient combination | 40% |
| ethylene glycol | 10% |
| nonylphenol-polyethylene glycol (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or the active-ingredient combination is intimately mixed with the additives. There is thus obtained a suspension concentrate from which can be prepared, by dilution with water, suspensions of the concentration required.

In the following biological Examples, a 'good action' signifies that the desired effect has resulted to the extent of at least 50 to 60%.

EXAMPLE 1

(a)
4-[3-Chloro-5-(1'-difluoro-2'-dichlorofluoroethyl)-2-pyridyloxy]-aniline 1.3 g of powdered potassium hydroxide are mixed with 10 ml of dimethyl sulfoxide. After the addition of 2.15 g of 4-nitrophenol, the mixture is stirred at 100° C. for 1 hour, and is then cooled to 50° C. There are subsequently added dropwise 5.1 g of 2,3-dichloro-5-(1'-difluoro-2'-dichlorofluoroethyl)-pyridine dissolved in 5 ml of dimethyl sulfoxide, and stirring is maintained in a nitrogen atmosphere at 120° C. for 5 hours. The reaction mixture is poured into ice water and extracted with toluene; the toluene phase is afterwards separated; washed with water, dried, and concentrated by evaporation to thus obtain 4-[3-chloro-5-(1'-difluoro-2'-dichlorofluoroethyl)-2-pyridyloxy]-nitrobenzene as a white powder, m.p. 100°–102° C.

5.3 g of 4-[3-chloro-5-(1'-difluoro-2'-dichlorofluoroethyl)-2-pyridyloxy]-nitrobenzene are mixed with 15 ml of concentrated hydrochloric acid. There are then added dropwise at 70°–75° C. 13.1 g of tin dichloride ($SnCl_2.2H_2O$) in 20 ml of concentrated hydrochloric acid, and the mixture is stirred at about 100° C. The reaction mixture is afterwards poured onto ice; it is subsequently rendered alkaline with sodium hydroxide solution (50% by weight of NaOH) and extracted with dichloromethane; the extract obtained is washed until neutral, dried, intensively concentrated by evaporation and filtered through silica gel. The resulting filtrate is concentrated by evaporation to obtain 4-[3-chloro-5-(1'-difluoro-2'-dichlorofluoroethyl)-2-pyridyloxy]-aniline in the form of white crystals, m.p. 87°–88° C.

(b) 42.3 g of 2,3-dichloro-5-(1'-difluoro-2'-dichlorofluoroethyl)-pyridine are dissolved in 30 ml of dimethyl sulfoxide. In the course of 30 minutes, this solution is stirred at 90° C., in a nitrogen atmosphere, dropwise into a mixture of 16.2 g of 4-aminophenol, 33.2 g of potassium carbonate and 140 ml of dimethyl sulfoxide. The reaction mixture is stirred for a further 2 hours under these conditions, and is then freed in a rotary evaporator in vacuo from the dimethyl sulfoxide. Dichloromethane and water are added to the residue, and the organic phase is repeatedly washed with water; it is afterwards dried, concentrated by evaporation to the extent of half and then filtered through silica gel. The solvent is largely evaporated off from the filtrate, and hexane is added to the residue. There is thus obtained 4-[3-chloro-5-(1'-difluoro-2'-dichlorofluoroethyl)-2-pyridyloxy]-aniline in the form of white crystals, m.p. 87°–88° C.

(c)
4-[3-Chloro-5-(1'-difluoro-2'-dichlorofluoroethyl)-2-pyridyloxy]-phenylisocyanate 1.5 g of 4-[3-chloro-5-(1'-difluoro-2'-dichlorofluoroethyl)-2-pyridyloxy]-aniline are dissolved in 30 ml of chlorobenzene, and the solution is added dropwise at 22° C., with stirring, to a solution consisting of 15 g of toluene containing 20% by weight of phosgene; 20 ml of dioxane and 60 ml of chlorobenzene, in the course of which the reaction temperature rises to 28° C. The reaction mixture is subsequently stirred at room temperature for one hour and for 90 minutes on a water-bath at 50° C. The reaction mixture is afterwards concentrated in a water-jet vacuum, and dried at 60° C. under high vacuum. There is obtained the title compound of the formula

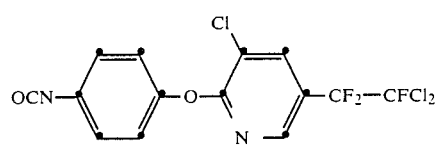

in the form of yellow oil.

EXAMPLE 2

3-[4-(3-Chloro-5-(1'-difluoro-2'-dichlorofluoroethyl)-2-pyridyloxy)-phenyl]-6-(2-chlorophenyl)-3,4-dihydro-2H-1,3,5-oxadiazine-2,4-dione With the exclusion of moisture, 3.7 g of chlorobenzoylisocyanate are added, with stirring, to 8.1 g of 4-[3-chloro-5-(1'-difluoro-2'-dichlorofluoroethyl)-2-pyridyloxy]-phenylisocyanate. The temperature is maintained at 120° C. for 12 hours, stirring being continued until the reaction mixture commences to solidify. When the formed crystal sludge has cooled to room temperature, it is triturated with hexane and subsequently filtered off with suction. The residue is recrystallised from toluene/chlorobenzene (10:1) to thus obtain the title compound of the formula

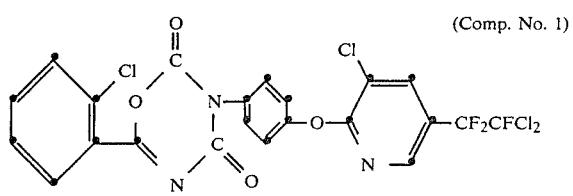

(Comp. No. 1)

having a m.p. of 198°–199° C.

The following compounds are obtained in an analogous manner:

EXAMPLE 3

Action against *Musca domestica*

50 g of freshly prepared CSMA nutrient medium for maggots are weighed off into each of a series of beakers. A specific amount of a 1% (by weight) acetonic solution of the respective active ingredient is transferred by pipette to the nutrient medium in each beaker. After a thorough mixing of the nutrient medium, the acetone is allowed to evaporate off for at least 20 hours. There are then deposited per active ingredient and concentration in each case 25 one-day-old *Musca domestica* maggots into each beaker containing the treated nutrient medium. After completion of pupation, the formed pupae are separated from the substrate by flushing with water, and are placed into vessels closed with perforated lids. The pupae flushed out per batch are counted (toxic effect of the active ingredient on the development of the maggots), and after 10 days the number of flies which have emerged from the pupae is determined.

Compounds according to Example 2 exhibit a good action in the above test.

EXAMPLE 4

Action against *Lucilia sericata*

1 ml of an aqueous preparation containing 0.5% of active ingredient is added to 9 ml of a culture medium at 50° C. About 30 freshly hatched *Lucilia sericata* maggots are then placed onto the culture medium, and after

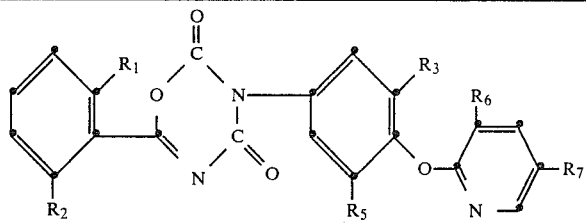

| Comp. No. | $R_1$ | $R_2$ | $R_3$ | $R_5$ | $R_6$ | $R_7$ | Physical data |
|---|---|---|---|---|---|---|---|
| 2 | Cl | H | H | H | H | $-CF_3$ | m.p.: 167–169° C. |
| 3 | Cl | H | H | H | Cl | $-CF_3$ | m.p.: 194–196° C. |
| 4 | F | F | H | H | Cl | $-CF_2CFCl_2$ | m.p.: 194–195° C. |
| 5 | Cl | H | Cl | Cl | Cl | $-CF_3$ | m.p.: 176–178° C. |
| 6 | F | F | Cl | Cl | Cl | $-CF_3$ | m.p.: 188–190° C. |
| 7 | F | F | H | H | Cl | $-CF_3$ | m.p.: 182–183° C. |
| 8 | F | F | Cl | Cl | H | $-CF_3$ | m.p.: 171–173° C. |
| 9 | F | F | $CH_3$ | H | Cl | $-CF_3$ | m.p.: 181–183° C. |
| 10 | Cl | H | H | H | H | $-CF_3$ | m.p.: 164–166° C. |
| 11 | Cl | H | Cl | Cl | H | $-CF_3$ | m.p.: 125–128° C. |
| 12 | Br | H | Cl | Cl | Cl | $-CF_3$ | m.p.: 181–183° C. |
| 13 | $CH_3$ | H | Cl | Cl | Cl | $-CF_3$ | m.p.: 181–182° C. |
| 14 | F | H | H | $COOCH_3$ | Cl | $-CF_3$ | m.p.: 185–187° C. |
| 15 | Cl | H | H | $COOCH_3$ | Cl | $-CF_3$ | m.p.: 181–182° C. |
| 16 | F | F | H | $COOCH_3$ | Cl | $-CF_3$ | m.p.: 191–193° C. |
| 17 | $CH_3O$ | H | H | $COOCH_3$ | Cl | $-CF_3$ | m.p.: 175° C. |
| 18 | $CH_3O$ | H | Cl | Cl | Cl | $-CF_3$ | m.p.: 188–190° C. |
| 19 | $CH_3O$ | H | $CH_3$ | H | Cl | $-CF_3$ | m.p.: 202–204° C. |
| 20 | $CH_3S$ | F | Cl | Cl | Cl | $-CF_3$ | m.p.: 155–175° C. |
| 21 | | | | | | | m.p.: 175–178° C. |

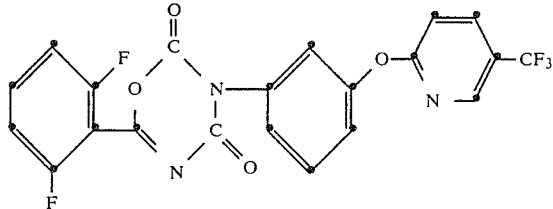

48 and 96 hours, respectively, the insecticidal action is determined by ascertaining the mortality rate.

Compounds according to Example 2 exhibit in this test a good action against *Lucilia sericata.*

EXAMPLE 5

Action against *Aedes aegypti*

Sufficient of a 0.1% acetonic solution of the respective active ingredient is transferred by pipette to the surface of 150 ml of water in a container to obtain a concentration of 12.5 ppm. After the acetone has evaporated off, 30–40 two-day-old Aedes larvae are placed into the container. The mortality rate is ascertained after 2 days and after 7 days.

Compounds according to Example 2 exhibit in this test a good action.

EXAMPLE 6

Insecticidal stomach-poison action

Cotton plants (about 20 cm in height) are sprayed with an aqueous active-ingredient emulsion (obtained from a 10% emulsifiable concentrate), the active-ingredient emulsion containing 100 ppm of the compound to be tested. After the drying of the applied coating, larvae of *Spodoptera littoralis* in the third larval stage and of Heliothis virescens in the third larval stage, respectively, are settled onto the cotton plants. The test is carried out at 24° C. with 60% relative humidity. At intervals in each case of 24 hours, an assessment is made of the mortality rate and also of development and shedding disturbances suffered by the exposed larvae.

Compounds according to Example 2 exhibit a good action in the above test.

EXAMPLE 7

Action on *Spodoptera littoralis* and *Heliothis virescens* (larvae and eggs)

Three cotton plants about 15–20 cm in height and grown in pots are treated with a sprayable liquid preparation of the respective active ingredient to be tested. After the drying of the applied coating, the potted plants are placed into a tin container of about 20 liters capacity, which is covered with a glass plate. The humidity inside the covered container is controlled in a manner ensuring that no condensation water is formed, and direct light falling onto the plants is avoided. The three plants are then infested in all as follows:

(a) 50 larvae of *Spodoptera littoralis* and *Heliothis virescens,* respectively, of the first larval stage;

(b) 20 larvae of *Spodoptera littoralis* and *Heliothis virescens,* respectively, of the third larval stage, and (c) two coatings of eggs of *Spodoptera littoralis* and *Heliothis virescens,* respectively (for this purpose, 2 leaves of a plant are in each case enclosed in a plexiglass cylinder sealed at each end with gauze); two coatings of eggs of Spodoptera, or a portion of a cotton-plant leaf on which are deposited eggs of Heliothis, are added to the enclosed leaves.

An evaluation, using untreated control plants as a comparison, is made after 4 and 5 days on the basis of the following criteria:

(a) number of larvae still alive,
(b) inhibition of larval development and shedding,
(c) damage caused by eating (scraping and hole damage),
(d) hatching rate (number of larvae which have emerged from the eggs).

Compounds according to Example 2 exhibit in the above test a good overall effectiveness at a concentration of 400 ppm.

EXAMPLE 8

Ovicidal action against *Spodoptera littoralis*

Eggs of *Spodoptera littoralis* deposited on filter paper are cut out of the paper and immersed in a 0.05% (by weight) solution of the active ingredient in an acetone/water mixture (1:1). The deposited eggs treated in this manner are then removed from this mixture, and placed at 28° C. with 60% relative humidity into plastics dishes. An assessment is made after 5 days of the hatching rate, that is, of the number of larvae which have developed from the treated eggs.

Compounds according to Example 2 exhibit a good action in the above test.

EXAMPLE 9

Action on *Laspeyresia pomonella* (eggs)

Deposited *Laspeyresia pomonella* eggs, not more than 24 hours old, are immersed on filter paper for 1 minute in an acetonic/aqueous solution containing 400 ppm of the active ingredient to be tested. After the drying of the solution of the eggs, they are laid out in Petri dishes and kept at a temperature of 28° C. The percentage hatching rate from the treated eggs is evaluated after 6 days.

Compounds according to Example 2 exhibit a good action in the above test.

EXAMPLE 10

Effect on reproduction of *Anthonomus grandis*

Adult *Anthonomus grandis,* which have been hatched no longer than 24 hours, are transferred, in groups each of 25 beetles, to cages having lattice walls. The cages containing the beetles are then immersed for 5 to 10 seconds in an acetonic solution containing 0.1% by weight of the active ingredient to be tested. After the beetles are again dry, they are placed, for copulation and oviposition, into covered dishes containing feed. Deposited eggs are flushed out with running water two to three times weekly; they are counted, disinfected by being placed for two to three hours into an aqueous disinfectant, and then deposited into dishes containing a suitable larval diet. An examination is made after 7 days to determine whether larvae have developed from the deposited eggs.

In order to ascertain the duration of the reproduction-influencing effect of the active ingredients tested, the oviposition of the beetles is observed during a period of about four weeks. The evaluation is on the basis of the reduction in the number of eggs laid and larvae hatched in comparison with that in the case of untreated control specimens.

Compounds according to Example 2 exhibit a good reproduction-reducing action in the above test.

EXAMPLE 11

Action against *Anthonomus grandis* (adults)

Two potted cotton plants in the 6-leaf stage are sprayed with aqueous emulsion preparations capable of wetting and containing 100 ppm of the active ingredient to be tested. After the drying of the applied coating (about 1½ hours), 10 adult beetles (*Anthonomus grandis*) are settled onto each plant. A plastics cylinder, the upper opening of which is covered with gauze, is placed over each treated plant infested with the test insects, in order to prevent the beetles from escaping. The treated plants are kept at 25° C. with about 60% relative humidity. An evaluation is made after 2, 3, 4 and 5 days with respect to the percentage mortality rate suffered by the test beetles (% dorsal position), and also with respect to the antifeeding effect, in each case compared with that occurring with untreated control batches.

Compounds according to Example 2 exhibit a good action in the above test.

What is claimed is:

1. A compound of the formula I wherein
R$_1$ is halogen, C$_1$–C$_4$-alkyl, C$_1$–C$_4$-alkoxy or C$_1$–C$_4$-alkylthio,
R$_2$ is hydrogen, halogen, C$_1$–C$_4$-alkyl, C$_1$–C$_4$-alkoxy or C$_1$–C$_4$-alkylthio,
R$_3$ and R$_4$ are each hydrogen, halogen or C$_1$–C$_4$-alkyl,
R$_5$ is hydrogen, halogen, C$_1$–C$_4$-alkyl or —COOR$_8$,
R$_6$ is hydrogen or halogen,
R$_7$ is mono- or polyhalogenated C$_1$–C$_4$-alkyl,
R$_8$ is hydrogen or C$_1$–C$_4$-alkyl, and
m is 1 or 2.

2. A compound of the formula I according to claim 1 wherein
R$_1$ is halogen or C$_1$–C$_4$-alkyl,
R$_2$ is hydrogen or halogen,
R$_3$ and R$_4$ are each hydrogen, halogen or C$_1$–C$_4$-alkyl,
R$_5$ is hydrogen, halogen, C$_1$–C$_4$-alkyl or —COOR$_8$,
R$_6$ is hydrogen or halogen,
R$_7$ is mono- or polyhalogenated C$_1$–C$_4$-alkyl,
R$_8$ is hydrogen or C$_1$–C$_4$-alkyl, and
m is 1 or 2.

3. A compound of the formula I according to claim 2, wherein
R$_1$ is halogen or C$_1$–C$_4$-alkyl,
R$_2$ is hydrogen or halogen,
R$_3$, R$_4$ and R$_5$ are each hydrogen, halogen or C$_1$–C$_4$-alkyl,
R$_6$ is hydrogen or halogen,
R$_7$ is mono- or polyhalogenated C$_1$–C$_4$-alkyl, and
m is 1 or 2.

4. A compound of the formula I according to claim 3, wherein
R$_1$ is halogen,
R$_2$, R$_3$, R$_4$ and R$_5$ are each hydrogen or halogen,
R$_6$ is hydrogen or chlorine,
R$_7$ is C$_1$–C$_2$-alkyl which is mono- or polysubstituted by fluorine and/or chlorine, and
m is 1 or 2.

5. A compound of the formula I according to claim 4, wherein
R$_1$ is chlorine or fluorine,
R$_2$ is hydrogen or fluorine,
R$_3$, R$_4$, R$_5$ and R$_6$ are each hydrogen or chlorine,
R$_7$ is —CF$_3$ or —CF$_2$CFCl$_2$, and
m is 1.

6. A compound according to claim 5 of the formula

7. A compound according to claim 5 of the formula

8. A compound according to claim 5 of the formula

9. A compound according to claim 5 of the formula

10. A compound according to claim 5 of the formula

11. A compound according to claim 5 of the formula

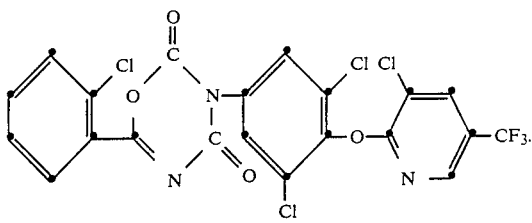

12. A compound according to claim 5 of the formula

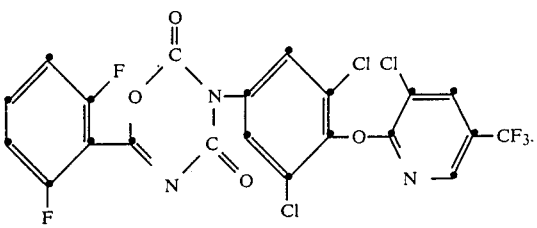

13. A compound according to claim 5 of the formula

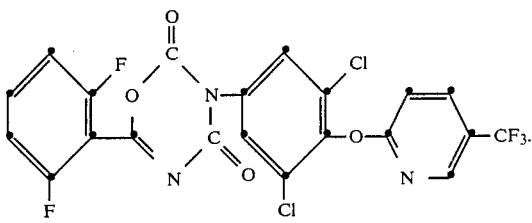

14. A pesticidal composition which contains, as active ingredient, a compound of the formula I

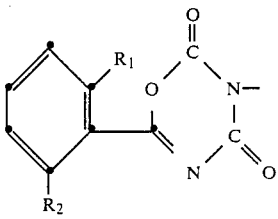 (I)

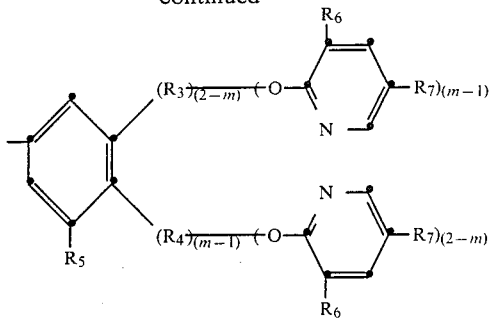

wherein
 $R_1$ is halogen, $C_1$-$C_4$-alkyl, $C_1$-$C_4$-alkoxy or $C_1$-$C_4$-alkylthio,
 $R_2$ is hydrogen, halogen, $C_1$-$C_4$-alkyl, $C_1$-$C_4$-alkoxy or $C_1$-$C_4$-alkylthio,
 $R_3$ and $R_4$ are each hydrogen, halogen or $C_1$-$C_4$-alkyl,
 $R_5$ is hydrogen, halogen, $C_1$-$C_4$-alkyl or —COOR$_8$,
 $R_6$ is hydrogen or halogen,
 $R_7$ is mono- or polyhalogenated $C_1$-$C_4$-alkyl,
 $R_8$ is hydrogen or $C_1$-$C_4$-alkyl, and
 m is 1 or 2,
together with suitable carriers and/or additives.

15. A method of controlling pests on animals and plants, which method comprises applying thereto or to the locus thereof an effective amount of a compound of the formula I

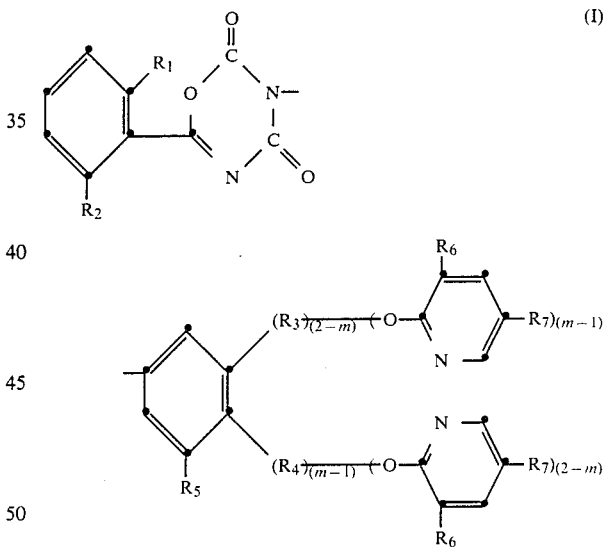 (I)

wherein
 $R_1$ is halogen, $C_1$-$C_4$-alkyl, $C_1$-$C_4$-alkoxy or $C_1$-$C_4$-alkylthio,
 $R_2$ is hydrogen, halogen, $C_1$-$C_4$-alkyl, $C_1$-$C_4$-alkoxy or $C_1$-$C_4$-alkylthio,
 $R_3$ and $R_4$ are each hydrogen, halogen or $C_1$-$C_4$-alkyl,
 $R_5$ is hydrogen, halogen, $C_1$-$C_4$-alkyl or —COOR$_8$,
 $R_6$ is hydrogen or halogen,
 $R_7$ is mono- or polyhalogenated $C_1$-$C_4$-alkyl,
 $R_8$ is hydrogen or $C_1$-$C_4$-alkyl, and
 m is 1 or 2.

16. A method according to claim 15 for controlling Arthropoda.

17. The method of claim 16, wherein the Arthropoda are selected from the group consisting of plant-damaging insects and arachnids.

* * * * *